(12) United States Patent
Yanof et al.

(10) Patent No.: US 11,737,829 B2
(45) Date of Patent: Aug. 29, 2023

(54) LOCALIZING A DEVICE RELATIVE TO AN INSTRUMENT

(71) Applicant: THE CLEVELAND CLINIC FOUNDATION, Cleveland, OH (US)

(72) Inventors: Jeffrey H. Yanof, Solon, OH (US); Karl West, Geneva, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 1143 days.

(21) Appl. No.: 16/349,321

(22) PCT Filed: Nov. 10, 2017

(86) PCT No.: PCT/US2017/060997
§ 371 (c)(1),
(2) Date: May 13, 2019

(87) PCT Pub. No.: WO2018/089732
PCT Pub. Date: May 17, 2018

(65) Prior Publication Data
US 2019/0290368 A1    Sep. 26, 2019

Related U.S. Application Data

(60) Provisional application No. 62/420,633, filed on Nov. 11, 2016.

(51) Int. Cl.
*A61B 34/20* (2016.01)
*A61B 90/00* (2016.01)
*A61B 17/22* (2006.01)

(52) U.S. Cl.
CPC .... *A61B 34/20* (2016.02); *A61B 2017/22042* (2013.01); *A61B 2034/2051* (2016.02); *A61B 2090/397* (2016.02); *A61B 2090/3983* (2016.02)

(58) Field of Classification Search
CPC .......... A61B 34/20; A61B 2017/22042; A61B 2034/2051; A61B 2090/397; A61B 2090/3983
See application file for complete search history.

(56) References Cited

U.S. PATENT DOCUMENTS 10,293,178 B2 *  5/2019  De Vries ............... A61N 5/1075
2013/0225943 A1 *  8/2013  Housing ................ A61B 5/062
                                                                600/409

OTHER PUBLICATIONS

Mohapatra, Abhisekh, et al. "Radiation exposure to operating room personnel and patients during endovascular procedures." Journal of vascular surgery 58.3 (2013): 702-709.
(Continued)

*Primary Examiner* — Joel Lamprecht
(74) *Attorney, Agent, or Firm* — TAROLLI, SUNDHEIM, COVELL & TUMMINO L.L.P.

(57) ABSTRACT

This disclosure relates generally to systems and methods for localizing a device relative to an instrument. A sensor of the instrument can be monitored for a change in signaling during a first transition of the device relative to the instrument. The sensor can further be monitored for another change in signaling provided by the sensor of the instrument in response to a second transition of the device relative to the instrument. A transition distance difference can be determined between the first transition and the second transition. A location of the device relative to the instrument can be determined based on a location of the instrument and the transition difference distance.

19 Claims, 7 Drawing Sheets

(56) References Cited

OTHER PUBLICATIONS

Panuccio, Giuseppe, et al. "Comparison of indirect radiation dose estimates with directly measured radiation dose for patients and operators during complex endovascular procedures." Journal of vascular surgery 53.4 (2011): 885-894.

Balter, Stephen, et al. "Fluoroscopically guided interventional procedures: a review of radiation effects on patients' skin and hair." Radiology 254.2 (2010): 326-341.

* cited by examiner

LOCALIZING A DEVICE RELATIVE TO AN INSTRUMENT

CROSS-REFERENCE TO RELATED APPLICATION

This application is a 371 of International Application No. PCT/US2017/060997, filed 10 Nov. 2017, which claims the benefit of priority of U.S. provisional patent application No. 62/420,633, filed on 11 Nov. 2016 and entitled LOCALIZING A DEVICE RELATIVE TO AN INSTRUMENT. The subject matter of each of the above-identified applications is incorporated herein by reference in its entirety.

TECHNICAL FIELD

This disclosure relates generally to systems and methods for localizing a device relative to an instrument.

BACKGROUND

In endovascular treatment of a patient, an endovascular device (e.g., a catheter or sheath) can be configured with an expandable member (e.g., a balloon deployable stent or self-expanding stent graft) and advanced over a guidewire located at a treatment site (e.g., a vascular lesion). At the treatment site, the endovascular device can be oriented to position the expandable member properly across the treatment site for deployment (e.g., inflation of the balloon or expansion of the stent graft). An existing approach for localizing the endovascular device during advancement over the guidewire uses radiopaque (RO) markers and fluoroscopic images. The endovascular device and guidewire can be employed with RO markers and a fluoroscope can be used to generate two-dimensional (2-D) real-time images of the patient while a RO marked endovascular device is guided over a RO marked guidewire to the treatment site.

However, use of fluoroscopy can lead to increased risks associated with endovascular treatment such as radiation-induced cancer as well as sub-optimal positioning of the endovascular device relative to the treatment site since fluoroscopy only provides a 2-D image while positioning the expandable member relative to the vascular lesion is a three-dimensional (3-D) process. Furthermore, use of fluoroscopy for guidance increases a procedure time required to position the endovascular device at the treatment time and increases a need for contrast dye (e.g., iodinated contrast material).

SUMMARY

This disclosure relates generally to systems and methods for localizing a device relative to an instrument.

As an example, a system includes an elongated instrument and an elongated sheath. The elongated instrument include at least one sensor at a distal end thereof and an electrical connection extending from the sensor to a proximal end of the instrument to communicate a sensor signal in response to the sensor detecting an electromagnetic field. The elongated sheath has a lumen extending longitudinally through spaced apart distal and proximal ends thereof. The lumen is dimensioned to permit axial movement of the instrument relative to the sheath within the lumen, the sheath including at least one marker band proximal the distal end of the sheath. The marker band is adapted to influence (e.g., interfere with or enable) the detection of the electromagnetic field by the sensor depending on an extent of axial alignment between the marker band and the sensor.

As another example, a system includes a guidewire including at least one sensor at a distal end thereof and an electrical connection extending from the sensor to communicate a sensor signal in response to the sensor detecting an electromagnetic field. An elongated sheath has a lumen extending longitudinally through spaced apart distal and proximal ends thereof. The lumen dimensioned to permit axial movement of the guidewire within the passage. The sheath includes at least one marker band fixed proximal the distal end of the sheath, the marker band circumscribing the lumen and adapted to influence the detection of the electromagnetic field by the sensor depending on an extent of axial alignment between the marker band and the sensor. A tracking system is configured to generate the electromagnetic field, the tracking system provides tracking data that represents the location of the sensor in a tracking coordinate system based on the sensor signal. The tracking data also specifies transitions in the sensor signal resulting from the influence of the marker band on the sensor signal. A location calculator determines a location of the sheath within the tracking coordinate system based on the tracking data. An output generator generates a graphical visualization representing the location of the guidewire and the location of the sheath with respect to a graphical representation of an anatomical structure.

As yet another example, a method includes sensing signaling by a sensor that is induced in response to an interrogation field. The sensor is fixed to an elongated instrument that is positionable within a patient's body. The method also includes detecting at least one transition in the sensed signaling provided by the sensor of during positioning of a distal end of a sheath relative to the instrument to influence detection of the interrogation field by the sensor. The method also includes determining a location of the sensor within a three-dimensional coordinate system based on the sensed signaling. The method also includes determining a location of the sheath within the coordinate system based on the detected at least one transition in the sensed signaling and the determined location of the sensor.

As still another example, a sensor of the instrument can be monitored for a change in signaling during a first transition of the device relative to the instrument. The sensor can further be monitored for another change in signaling provided by the sensor of the instrument in response to a second transition of the device relative to the instrument. A transition distance difference can be determined between the first transition and the second transition. A location of the device relative to the instrument can be determined based on a location of the instrument and the transition difference distance.

BRIEF DESCRIPTION OF THE DRAWINGS

FIGS. 5A-E illustrate an example for localizing a catheter relative to a guidewire.

FIGS. 6A-G illustrate an example for positioning a balloon deployable stent relative to a target site.

DETAILED DESCRIPTION

This disclosure relates generally to systems and methods for localizing a device relative to an instrument. The systems and methods described herein can be used for tracking the location and orientation of a device (e.g., a sheath) relative to an instrument.

For example, the instrument is a guidewire that includes one or more sensors at a distal end thereof. Each sensor communicates sensor signals in response to an interrogation field (e.g., an electromagnetic field). An electrical connection extends from each sensor to communicate its sensor signal induced in response to the sensor detecting an electromagnetic field. For example, the sensor is coil and the electromagnetic field induces the sensor signal. An elongated sheath (e.g., a catheter or cannula) has a lumen extending longitudinally through spaced apart ends thereof. The lumen is dimensioned to permit axial movement of the guidewire within the passage. The device, however, does not itself include sensors or otherwise communicate signals to enable localization. The device includes one or more field-influencing objects that can affect detection of the field by an adjacent sensor of the instrument. For example, each field-influencing object is implemented as a marker band near a distal end of the sheath. The marker band circumscribes the lumen and is adapted to influence the detection of the electromagnetic field by the sensor depending on an extent of axial alignment between the marker band and the sensor.

As further example, a tracking system is configured to generate the electromagnetic field. The tracking system also provides tracking data based on the sensor signal provided by each sensor in response to the electromagnetic field. The tracking data represents the location of the sensor in a tracking coordinate system based on the sensor signal. The tracking data also specifies transitions (e.g., changes) in the sensor signal resulting from the influence of the marker band when in a prescribed alignment (e.g., circumscribing) with respect to a give sensor. The tracking system determines the position of each sensor in a tracking coordinate system in response to the sensor signals, which can be used likewise to localize the position of the instrument itself.

The system also includes a location calculator that determines a location of the sheath within the tracking coordinate system based on the tracking data. As a further example, the sheath (e.g., an endovascular device, such as a catheter or cannula) includes a body lumen through which the instrument (e.g., a guidewire) is positioned to traverse axially. As the distal end of the instrument, which includes one or more sensors, moves within the distal end of the sheath, which includes one or more marker bands, the sensor signals exhibit transitions in signaling due to the influence of the marker band. One or more transitions in the sensor signals can thus be identified and used by the location calculator to determine a position of the sheath relative to the guidewire/instrument and, in turn, determine an absolute position of the device in the coordinate system of the tracking system. An output generator can then generate a graphical visualization (e.g., a three-dimensional visualization) representing the location of the guidewire and the location of the sheath with respect to a graphical representation of an anatomical structure.

The systems and methods disclosed herein enable accurate tracking of the endovascular device, even though it may not include sensors or otherwise communicate signals to enable its localization directly by the tracking system. That is, by including field-influencing objects on the endovascular device that is used in conjunction with a guidewire that includes sensors localizable by the tracking system, the position of the endovascular device may be determined within acceptable accuracy. This helps to improve a navigation time of the endovascular device to the treatment site and substantially reduces a risk of incorrectly positioning the device and thereby improves the delivery and/or treatment at target site.

Figure 1A:
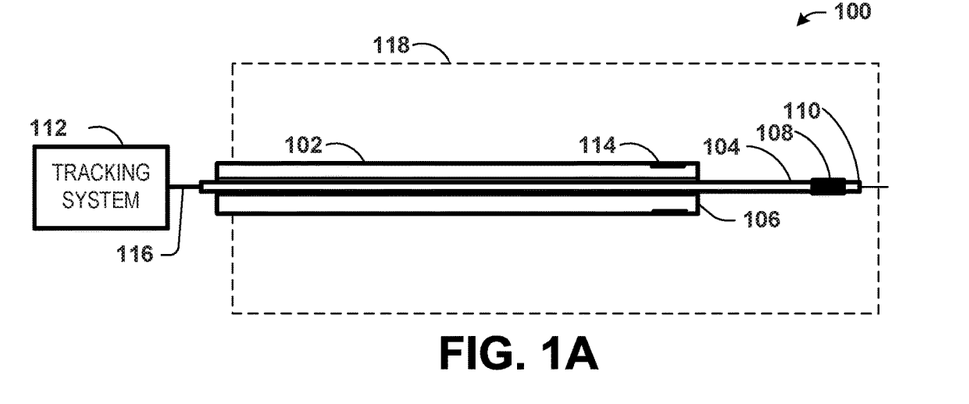
FIGS. 1A, 1B and 1C illustrate an example of a system for localizing a device relative to an instrument shown in different relative axial positions.
Figure 1B:
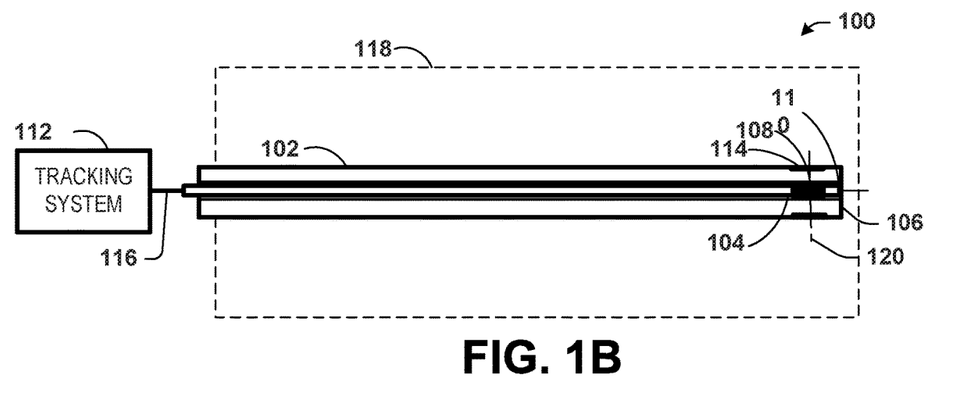
Figure 1C:
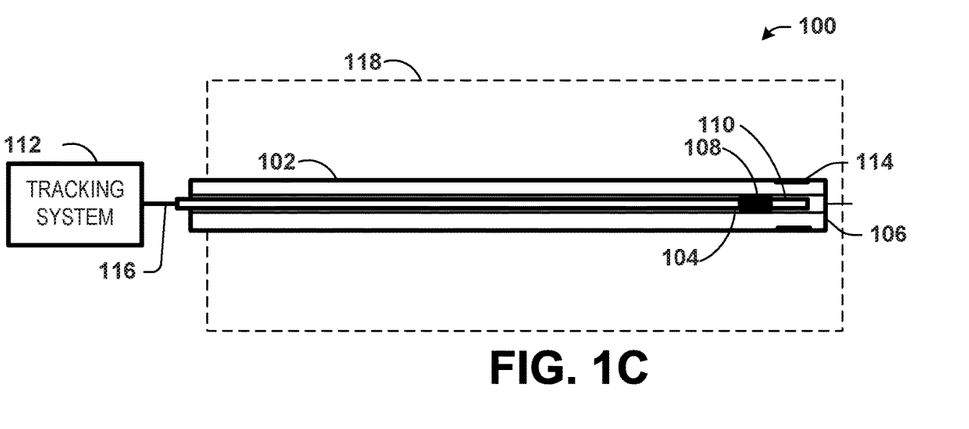

FIGS. 1A, 1B and 1C illustrate an example of a system 100 for localizing a device 102 relative to an instrument 104, shown in different relative axial positions. In FIG. The device 102 could be a guidewire and the instrument 104 can be a sheath, such as a catheter, cannula or other elongated instrument through which the device may traverse generally axially. The system 100 can be employed during a medical procedure, such as an angioplasty procedure, aneurysm procedure, aortic stenosis procedure, etc. The system 100 enables three-dimensional (3D) localization of the device 102 relative to the instrument 104 in a coordinate system.

In the example of FIG. 1, the instrument 104 can include one or more sensors 108. Each of the sensors 108 can include a sensor coil of an electrically conductive wire. The sensor coil 108 can includes a predetermined number of turns and be of a given axial length extending longitudinally on an exterior portion of the distal end 110 of the instrument 104. Each sensor 108 can be electrically connected to communicate sensor signal to a tracking system 112, such as by an electrical connector 116. For example, each sensor is implemented as a 5 degree of freedom sensor or a 6 degree of freedom sensor, such as the types that are commercially available from Northern Digital Inc. of Ontario, Canada.

The device 102 is demonstrated as an elongated sheath that includes one or more marker bands (MBs) 114. For example, each marker band 114 includes a cylindrical body of material that circumscribes (completely or partially surrounds) the lumen of the sheath 102. The marker band 114 is adapted to influence the detection of the electromagnetic field by the sensor 108 depending on an extent of axial alignment between the marker band and the sensor. For instance, the marker band can be formed of a magnetic shielding material or a magnetic material (e.g., a permanent magnet). In order to maximize the influence on the sensor 108, the radial distance between the marker band 114 and the sensor should be minimized. The one or more MBs 114 can be affixed to surface of the device 102 to prevent dislodgment, for example, during the medical procedure (e.g., advancement, navigation and retraction of the device 12 through the endovascular structures). Alternatively or additionally, the MB 114 may be disposed or integrated within the sidewall. For example, the MBs may be integrated into the sidewall itself or be inserted into recesses at one or more distal end locations, such as bands or loops extending circumferentially around the sidewall of the device 102. The axial length of the MB 114 may approximate the axial length of the sensor 108 to enable corresponding field influence (e.g., increasing or inhibiting) on the sensor 108. In some examples, the cylindrical body has a rectangular cross sectional shape. In other examples, such as when it is formed of a magnetic material (e.g., it produces a magnetic field), the cylindrical body is configured with a tapered (e.g., trapezoidal) cross section extending from an outer surface and tapering to a radially inner surface (see, e.g., FIG. 6).

The tracking system 112 can include one or more field generators to generate an EM field within a volume of 3D space 118. The EM fields generated in the patient space can induce currents in the EM coils. These induced signals from the sensor coils 108 are supplied to the tracking system 112 via its connection. The tracking system 112 determines a location and orientation of the instrument 104 in the patient space based the induced signals provided by each respective sensor coil. The tracking system 112 thus can determine the location and orientation of the instrument 104 in real time as the instrument 104 is being maneuvered through the 3D volume 118. As an example, the tracking system 112 can track the instrument 104 through the endovascular structures of the patient when positioned within the 3D field volume 118. Examples of a tracking system 112, sensors 104 and EM field generator that can be used in the system 100 are commercially available from Northern Digital Inc. of Ontario, Canada.

As mentioned, the influence on the detection of the electromagnetic field by the sensor 108, which is used to determine the location of the instrument 104 and the device 102, depends on the extent of axial alignment between the marker band and the sensor. By way of example, the device 102 can be advanced or retracted in an axial direction relative to the instrument 104. As shown in FIG. 1A, the distal end 110 of the instrument 104 extends beyond the distal end 106 of the sheath. In this position (FIG. 1A), the MB 114 is not aligned with any sensor 108 and thus does not influence its sensing of the field.

During relative axial movement, the one or more MBs 114 can be transitioned to an axially aligned position with respect to a respective sensor 108 of the instrument 104, such as shown in FIG. 1B. In this example, the axial alignment between the MB 114 and the sensor 108 is demonstrated by the center the MB 114 being substantially aligned with the center of the sensor such that the MB circumscribes the sensor. For example, the alignment between MB 114 and the sensor 108 is demonstrated by a virtual plane 120 that extends through the device 102 and instrument 104 perpendicular to the longitudinal axis 122 of both device 102 and instrument 104 and that intersects the approximate centers of the MB 114 and the sensor 108. With such alignment, the MB 114 influences (e.g., shields or otherwise affects) the strength of the signal being induced at the adjacent sensor 108.

For example, the tracking system 112 detects the interference in response to changes in the sensor signal (e.g., a reduction or increase in signal amplitude) and, based on the known location of each MB along the end of the device 102, derives a location of the device in the patient space based on the location of the sensor 108 determined by the tracking system. The tracking system 112 can detect a first transition in the sensed signaling from a first type of sensor signal provided in response to detecting the field to a second type of sensor signal provided in response to interference with sensing the induced signaling in response to the field. The tracking system 112 can also detect a second transition in the sensed signaling from the second type of sensor signal to the first type of sensor signal.

As a further example, prior to the interference due to alignment of an MB 114 with a respective sensor 108 (as in FIG. 1A or 1C), the sensor can provide a first type of signal, which the tracking system can utilize to derive a 3D position of each such sensor. When the one or more MBs 114 interfere with a respective sensor 108, as in FIG. 1B, the respective sensor 108 can provide a second type of signal (e.g., a low amplitude signal or an otherwise modified sensor signal). The tracking system 112 can identify the location of the sensor 108 in response to detecting transitions between the first and second types of signals, as the transition and position before and/or after the transition thus identifies the location of the MB that caused the interference. Since the location of the MBs relative to the end of the device 102 is known a priori, the 3D position of the end portion of the device can thus be derived and stored in memory along with the location of the sensors.

Additionally, from a position of interfering alignment between a given MB and sensor 108 (FIG. 1B), the device 102 can be retracted a given distance in an opposite direction of the advancement until the one or more MBs 114 are not substantially interfering with the respective sensor 108. Alternatively, the instrument 102 can be subsequently advanced further a given distance along a length of the instrument 104 until the one or more MBs 114 are not substantially interfering with the respective sensor 108. The tracking system 112 thus can detect when interference with each of the MBs 114 begins and ends by monitoring signals generated by the respective sensor 108 while the device 104 is being retracted or advanced. The changes in the sensor signal may also provide an indication of the direction of the MBs relative to a given sensor.

As mentioned, the tracking system 112 can also detect when the one or more MBs 114 are not substantially interfering with the respective sensor 108 by monitoring the sensor signal for a change in signaling from the second type to the first type (e.g., during retraction) or from the second type back to the first type (e.g., during the subsequent advancement) provided by the respective sensor 108 during movement of the device 102 relative to the instrument 104 corresponding to a second transition. The tracking system 112 may also determine a transition difference distance between the first transition and the second transition by calculating a distance between the determined location of the instrument and a location at which the signal provided from the respective sensor 108 changed from the first type to the second type. The tracking system 112 thus can determine a location of the device 102 in the patient space based on the transition difference distance and the determined location of the instrument 104. As a result, the tracking system 112 can determine the location of the end portion of the device 102 relative to the instrument 104 based on detected transitions.

Each MB 114 can be configured to produce a magnetic field (e.g., formed of a permanent magnet) or be configured to inhibit transmission of electromagnetic fields (e.g., referred to as a shield type MB). Shield type MBs can be fabricated from thin magnetic shielding material with high magnetic permeability, such as mu-metal. Magnetic type MBs can be fabricated from a variety of magnetic materials, such as a ferromagnetic material. As a further example, the MBs may be formed of or otherwise coated with a biocompatible material.

In another example, the magnetic and/or shield type MBs can be encapsulated or contained within a thin biocompatible plastic layer (as an outermost coating layer or housing), while maintaining a low device profile. The thin biocompatible plastic layer can include anchoring clasps or barbs for rigid adherence with an outer layer of the device 102 during maneuvers of the device 102 through the endovascular structures of the patient. In an additional example, the MBs 114 can function as radio opaque (RO) markers if there is a step or sequence in the medical procedure that may require use of fluoroscopy based images. This can facilitate to application of the MBs to existing endovascular devices.

Additionally or alternatively, a similar layer of biocompatible material may likewise be applied over each sensor 108.

The system 100 of FIG. 1 can be employed to localize the device 102 relative to the instrument 104. Accurate localization of the device 102 allows the device 102 to be accurately tracked as its being navigated through an endovascular structure of the patient. Accurate localization also facilitates application of therapy and/or implantation of a device at a desired target site. Thus, the system of 100 substantially reduces a risk of incorrectly positioning an expandable member or other implantable device relative to the target site, such as for application of therapy and/or delivery of an implantable object.

Figure 2:
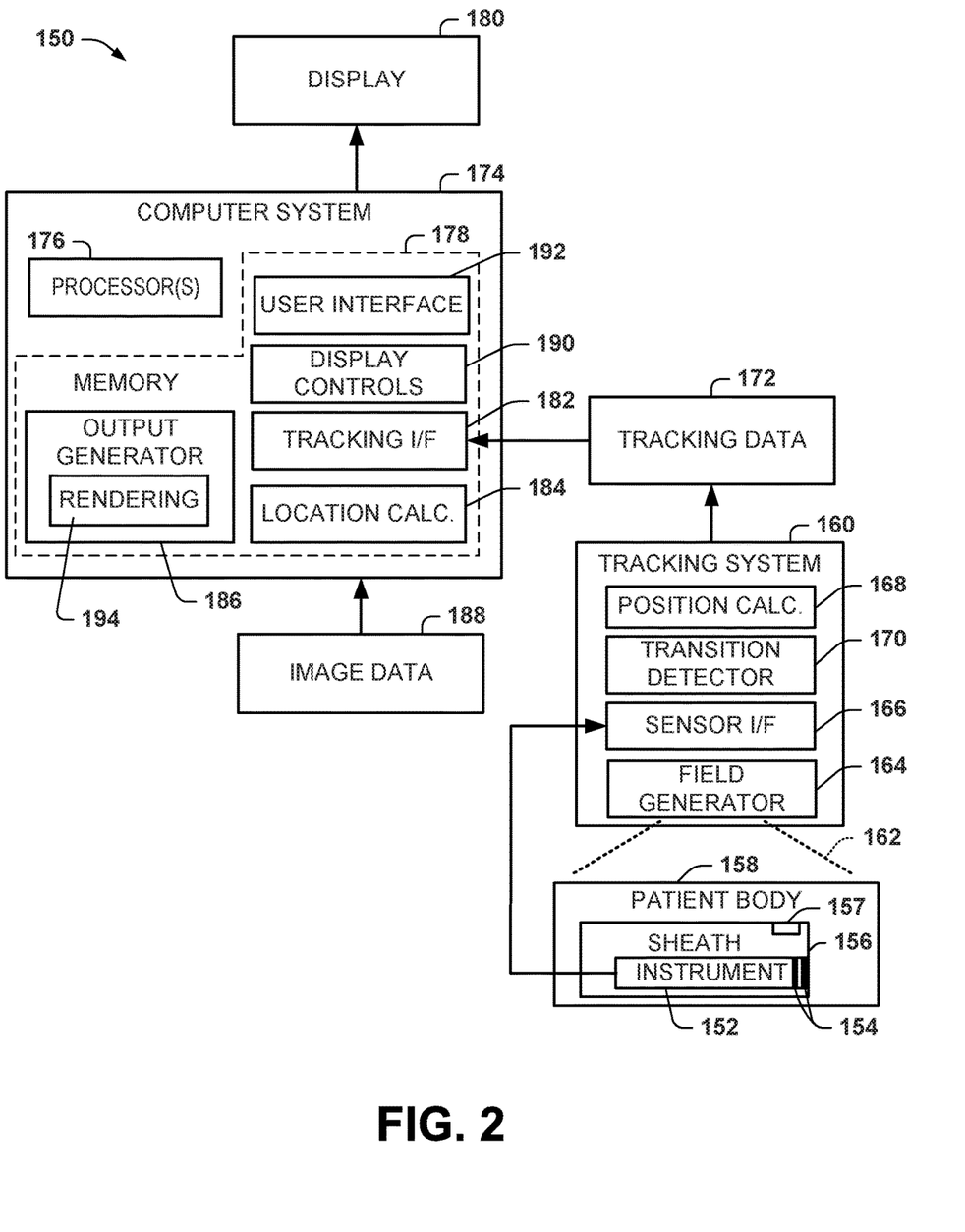
FIG. 2 illustrates an example of a system block diagram of a system for localizing a device relative to an instrument.

FIG. 2 depicts an example of a navigation system 150 that can be utilized to provide image-based guidance. The system 150 provides guidance in the form of a graphical image that is produced on a display 180 to visualize includes a graphical representation of an instrument 152 and endovascular device 156 localized with respect to patient anatomy that is also rendered in the visualization. The instrument (e.g., a guidewire) 152 includes one or more sensors 154 distributed along its length. For example, an arrangement of one or more sensor coils 154 can be disposed on the distal end of the guidewire 152 such as disclosed herein.

The device 156 may be implemented as a sheath (e.g., a catheter or other device) 156 that includes a lumen through which the guidewire 152 axially traverses. The sheath 156 includes an arrangement of one or more field-influencing objects (e.g., marker bands) 157 disposed on the distal end of the sheath, such as disclosed herein. Each marker band is adapted to influence (e.g., by interfering with or enhancing) the detection of an electromagnetic field by a respective sensor. As disclosed herein, the influence on the sensing by the sensor 154 depends on an extent of axial alignment between a given marker band and a given sensor. In the example of FIG. 2, the guidewire and sheath are schematically illustrated within a patient's body 158.

The system 150 also includes a tracking system 160 such as the tracking system 112 discussed above with respect to FIG. 1. The tracking system 160 is configured to provide tracking data 172 that is used to determine the position of the instrument 152 and sheath 156 in a 3D coordinate system. In the example of FIG. 2, the tracking system includes one or more field generators 164 to provide an electromagnetic (a non-ionizing) field 162 to a region (a volume) of interest that includes the patient's body 158, including anatomical structures (e.g., vasculature), where the distal ends of the instrument 152 and sheath are positioned. An example tracking system 154 is commercially available from Northern Digital, Inc., of Ontario, Canada.

Each of the one or more sensors 154 is connected to a sensor interface 166 of the tracking system to provide a corresponding sensor signal that is induced in response to the field 162. The tracking system 160 also includes a position calculator 168 to compute position and orientation of each sensor in a tracking coordinate system for the volume of interest based on each sensor signal received via the interface 166. The tracking system 160 can provide the tracking data 172 at an output sample rate (e.g., sixty samples per second) for each sensor sufficient to enable substantially real time determination of sensor location (e.g., to provide a vector describing sensor position and orientation). The tracking data 172 thus can include real time tracking data acquired by the tracking system 160 representing the position and orientation of the sensors in the tracking coordinate system of the tracking system 160 over time.

The tracking system 160 also includes a transition detector 170 to identify transitions in the sensor signal corresponding to periods when the marker band influences a given sensor. For example, the transition detector 170 can identify a transition may be detected base a measure of a signal to noise ratio (SNR) decreasing below a predetermined value, which can be preprogrammed or determined during operation, over a number of sample intervals. The transitions can correspond to changes in the expected sensor signal, such as occurs during alignment of the marker band 157 with a respective sensor 154, as disclosed herein. For example, where the marker band 157 inhibits the sensing of the field (e.g., by magnetic shielding), the transition corresponds to change from an expected full signal level, which can be used to localize the sensor, to a decreased signal amplitude (e.g., below a prescribed threshold) or another transition from the decreased signal amplitude to the expected full signal level.

The tracking system 154 can provide the tracking data with an output sample rate to enable computation of real time positioning of the instrument 152 to which the sensor is attached as well as the sheath 154. The tracking system 160 thus can combine information about the identified transitions and the calculated position and orientation to provide the tracking data can also include an indication of transitions in the sensor signals, as identified by the transition detector 170. For example, the indication of the presence or absence of transitions can be appended to each frame of the tracking data for further processing by a location calculator 184. The location calculator 184 determines a location of the sheath within the tracking coordinate system based on the tracking data.

The computer system 174 includes one or more processors 176 and memory 178. The processor 176 executes instructions stored in the memory 178 to perform the functions disclosed herein. In the example of FIG. 2, the functions include the location calculator 184, a tracking interface (e.g., an application programming interface) 182, an output generator 186, display controls 190 and a user interface 192. While in this example, the location calculator 184 is implemented in the computer system 174, which is connected with the tracking system 160 via a tracking interface, in other examples, the location calculator and other functionality described within the computer system 174 can be integrated with the tracking system functionality—either within the tracking system or the computer system. The location calculator 184 further can utilize geometry data that characterizes the relative geometry and dimensions of the sheath and the instrument for at least configurations where the detected transitions occur. The geometry information may be stored in the memory for the sheath 156 and/or instrument 152 to enable the location of the distal end of the sheath to be determined from the detected transitions. Thus, the tracking system can thus localize the sheath (or other device) 156 relative to the instrument in the patient space or another coordinate system (e.g., the coordinate system of the tracking system) even though the sheath itself does not include sensors electrically connected to the tracking system 160 as is the case of the sensors on the instrument 152.

As an example, the geometry information for the sheath 156 and instrument 152 can be implemented as a model corresponding to an analytical or parametric representation of the sheath, which may be a generally rigid surgical instrument or an articulated instrument that includes a flexible tip such as wires, catheters and the like. Accordingly the implicit model will vary according to the type of instrument or other object that is being tracked within the patient's anatomy. In addition to parameterizing the geometry of the sheath 156 and instrument 152, model data can also be programmed to model other properties of the objects (e.g., resilience and/or ductility), which the output generator may utilize to adjust the resulting visualization.

The output generator 186 can provide the output visualization to a display 180 to visualize a graphical representation of the instrument 152 and sheath device 156 localized with respect to patient anatomy that is also rendered in the visualization. The output generator 186 (or other functions not shown) can translate the anatomy into the coordinate system of the tracking system or translate the position information derived from the tracking data (and/or the tracking data itself) into the coordinate system of patient anatomy. For example, the patient anatomy can be stored in the memory 178 as a patient-specific implicit model of anatomy. The patient-specific implicit model can be generated based on image data 188 acquired for the patient to define geometry of the anatomical structure of the patient. The image data 188 used to generate the patient-specific implicit model can be acquired before the intraoperative procedure that is being tracked by the tracking system. For example, the image data 188 can be acquired as part of a preoperative planning stage and may 3D images of patient anatomy, including one or more endovascular structures of the patient. In one example, a computed tomography (CT) imaging modality is used prior to the procedure to acquire the image data of the patient. In other examples, one or more other imaging modalities may be used.

Once the relevant data is in a common coordinate system, the output generator 186 can generate the visualization data based on the tracking data 172, image data 188 and position data that is computed (by location calculator 184). The memory 178 can also store the model data for the geometry of the instrument 152 and the sheath 156 to facilitate the rendering of the visualization. As a further example, the output generator 186 includes a rendering method 194 programmed to produce a three-dimensional plot corresponding to the visualization data. Various types of rendering software (e.g., commercially available or proprietary) can be utilized and implemented as the rendering method 194 and can vary according to the type of models generated for use by the output generator 186.

The display controls 190 that can control the output that is provided in real time based on the tracking data (e.g., intraoperatively). The display controls 190 can be configured to selectively generate any number of one or more displays concurrently on one or more screens, each of which can include a different view of the object and the anatomic structure. The respective views can be selected automatically such as by default parameters or it can be adjusted in response to the user input just as can be provided a user interface 192. This display controls 190 can further control a viewing angle for each of the visualizations of the anatomical model and the object that are presented to the user. In examples where the structures in each visualization are virtual renderings based on implicit models, the resulting output visualization is not constrained to any particular viewing angle or type of visualization.

In some examples, the display controls 190 can compute and display task-specific visualizations, such as may include an optimal view for a particular task (for example, cannulating a renal artery). For example, when cannulating a vessel, it is useful to visualize the vessel and wire without distractions or obstructions. The output generator is able to create this visualization since each vessel and each device are virtual renderings. Thus, the display controls can instruct the rendering method 194 to produce nearly any visualization in two- or three-dimensional space, which can be rendered rapidly based on the tracking data 172. The system 150 can provide real-time visual feedback as the instrument 152 and sheath 156 are guided through endovascular structures of the patient 158 based on a relative location of the instrument 152 determined by the tracking data 172 and the sheath 156 based on detected transitions associated with the tracking information.

The navigation system can generate a 3-D anatomical model based on the acquired image data and display the generated 3-D anatomical model on a display. The 3-D anatomical model can be related to location information characterizing a position and/or orientation determined for the instrument 152 directly and the sheath 156, indirectly. Icons or other graphical representations of the instrument 152 and the sheath 156 can be superimposed over the generated 3-D anatomical model to allow tracking of the instrument and the sheath 152 on the display 180. The location of the sheath 156 relative to the instrument 152 can be visualized on the display 180. As a further example, when the instrument 152 is implemented as a medical guidewire for traversing the patient's vasculature in a minimally (or low) invasive manner, the visualization of the relative location of the sheath 156 and instrument 152 on the display 180 substantially improves an accuracy of tracking of the devices during a medical procedure. For example, such tracking can also enable deployment of an expandable member of the sheath (e.g., a balloon catheter) relative to the treatment site via the device 102, such as to enable accurate implantation of a stent, graft or other expandable device.

Figure 3:
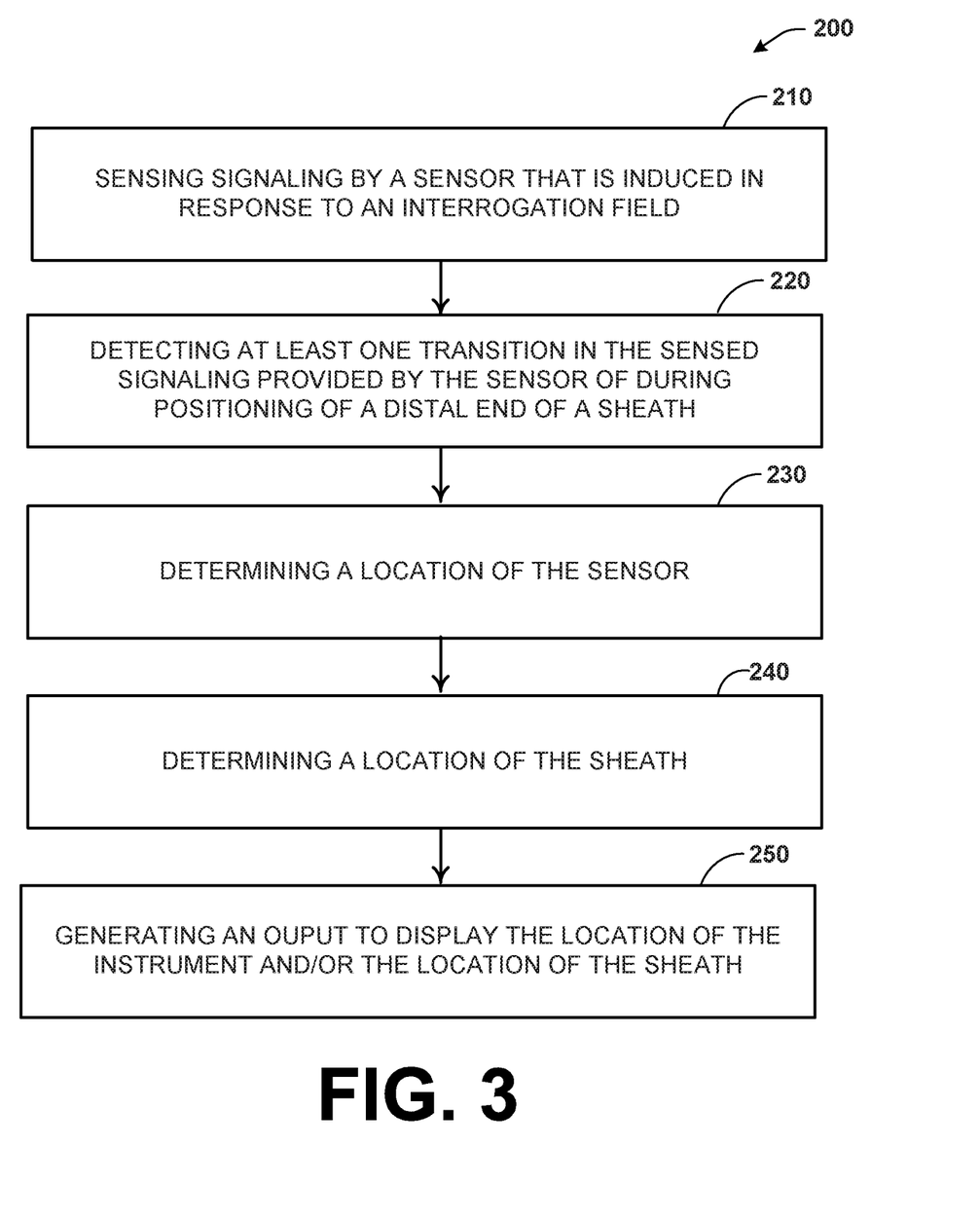
FIG. 3 depicts a method for localizing a device relative to an instrument.
Figure 4:
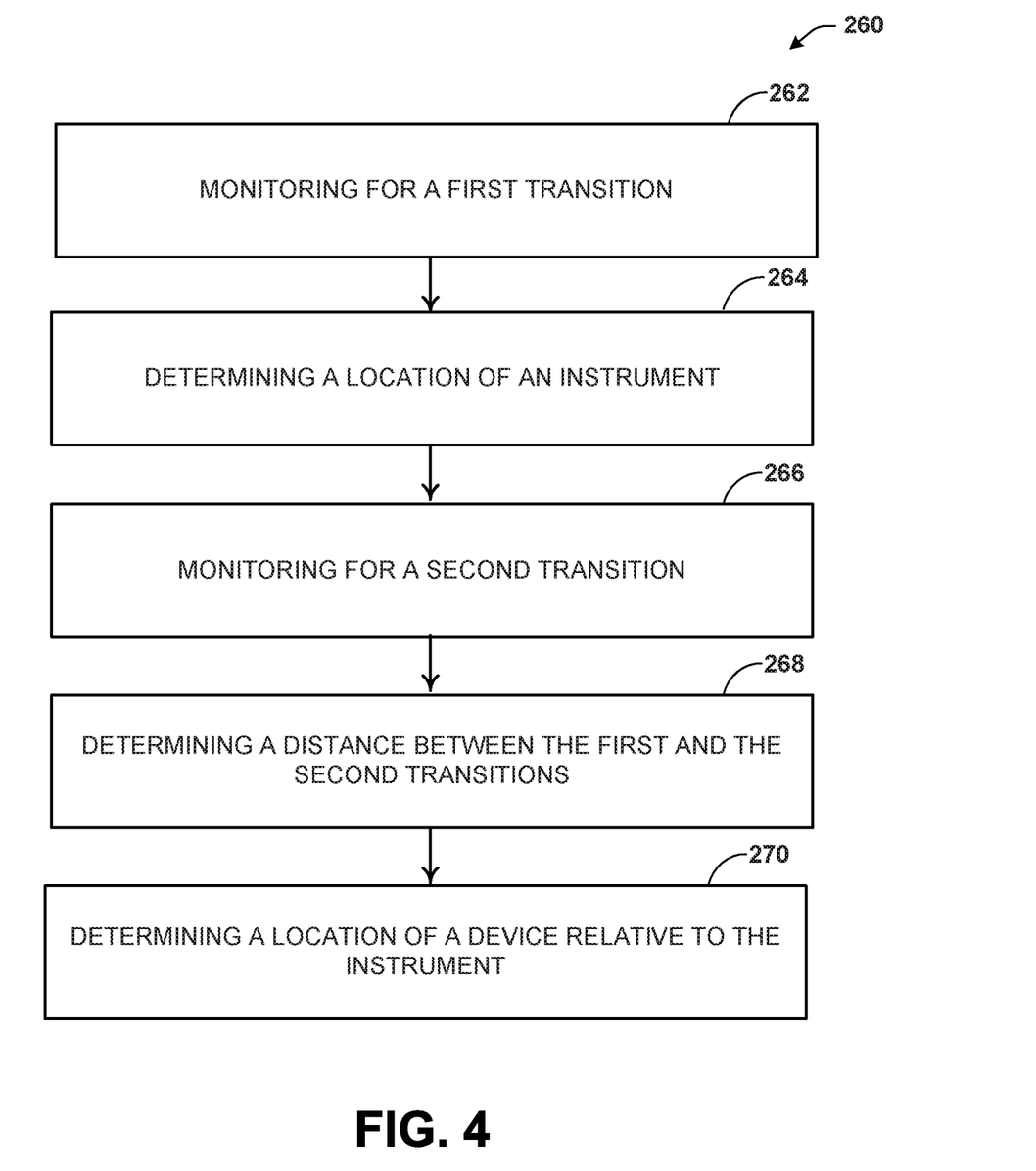
FIG. 4 depicts a method for localizing a device relative to an instrument.

In view of the foregoing structural and functional features described above, example methods will be better appreciated with reference to the methods of FIGS. 3 and 4. While, for purposes of simplicity of explanation, the method is shown and described as executing serially, it is to be understood and appreciated that method is not limited by the illustrated order, as some aspects could, in other examples, occur in different orders and/or concurrently with other aspects from that shown and described herein. Moreover, not all illustrated and described features may be required to implement a method.

At 210, the method includes sensing signaling by a sensor (e.g., 108, 154) that is induced in response to an interrogation field (e.g., field 162). For example, an electromagnetic field can be generated (e.g., by a field generator 112 or 164) to induce the signaling of the sensor. The sensor is fixed to an elongated instrument (e.g., guidewire or other instrument 104, 152) that is positionable within a patient's body. For example, the instrument is a guidewire and the sheath has an elongated body having a lumen to receive and permit axial movement of the guidewire within the lumen. The elongated body thus can include one or more marker bands circumscribing the lumen proximal a distal end of the sheath. As mentioned, the marker band influences the interrogation field detected by the sensor depending on an extent of axial alignment between the marker band and the sensor within the lumen. The marker band, for example, may include a magnetic shielding material or a magnetic material.

At 220, one or more transitions are detected (e.g., by a tracking system 112 or 160) in the sensed signaling provided by the sensor of during positioning of a distal end of a sheath (e.g., 102 or 156) relative to the instrument to influence detection of the interrogation field by the sensor. For example, the transition may include a first transition in the sensed signaling that changes from a first type of sensor signal provided in response to the sensor detecting the interrogation field to a second type of sensor signal provided in response to interference with the induced signaling. Thus, even though the interrogation field still persists, the marker band operates to shield the sensor from sensing the field—at least blocks enough to detect the transition. The detected transition at 220, also may include a second transition in the sensed signaling corresponding to a change from the second type of sensor signal (low amplitude) to the first type of sensor signal (high amplitude). The location of the sheath can be determined for each of the transitions.

At 230, a location of the sensor is determined (by tracking system 112 or 160) within a three-dimensional coordinate system based on the sensed signaling. At 240, a location of the sheath within the coordinate system is determined (by calculator 184 or tracking system 112 or 160) based on the detected transition in the sensed signaling and the determined location of the sensor. The location of the device can be determined, for example, by calculating a distance vector in the three-dimensional coordinate system corresponding to a distance between the determined location of the instrument and a location at which the detected transition in the induced signaling occurs. The location of the sheath thus can be determined based on the calculated distance vector and predetermined dimensions of the sheath (e.g., stored in memory as model data that represents geometry of the sheath).

At 250, an output visualization to a display is generated (e.g., by output generator 186). The output visualization including the determined location of the instrument and the determined location of the sheath superimposed with respect to a graphical representation of an anatomical structure. The anatomical structure can be as an anatomical model that is generated based on acquired image data of one or more endovascular structures.

FIG. 4 depicts another example method 260 for localizing a device (e.g., the device 102, as illustrated in FIG. 1) relative to an instrument (e.g., the instrument 104, as illustrated in FIG. 1). The method 260 can be implemented, for example, by a tracking system (e.g., the tracking system 112, as illustrated in FIG. 1). At 262, a sensor of the instrument can be monitored for a change in signaling during a transition of the device relative to the instrument corresponding to a first transition. For example, each sensor on the instrument can be electrically connected with the tracking system via an electrical conductor extending from the sensor through the instrument (e.g., guidewire) to the tracking system. At 264, a location of the instrument can be determined in response to detecting the change in signaling provided by the sensor. At 266, the sensor of the instrument can be monitored for another change in signaling during another transition of the device relative to the instrument corresponding to a second transition. At 268, a transition distance difference can be determined between the first transition and the second transition. At 270, a location of the device relative to the instrument can be determined based on the determined location of the instrument and the determined transition difference distance.

Figure 7:
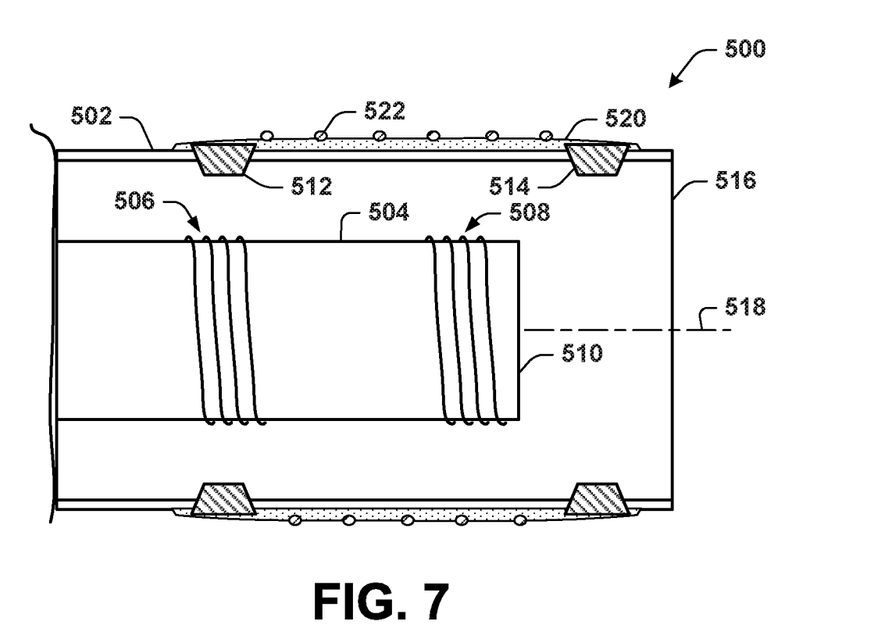
FIG. 7 depicts an example of part of a system illustrating an instrument positioned within a device.

As part of the method 200 or 260, for example, the sheath can be moved relative to the instrument to position the marker band in axial alignment with the sensor and circumscribe the sensor. For example, the sheath may be axially advanced or retracted relative to the instrument (guidewire) located within the lumen to cause the at least one transition. At such axially aligned position, the signaling that is induced in response to the electromagnetic field is mitigated (or otherwise changed) to enable detection of the transition in the sensed signaling. A message can be provided (e.g., on a display and/or audio) to indicate the detected transition in the sensed signaling. After the location of the sheath is determined with respect to the location of the instrument, the method can also include physically fixing the instrument with respect to the sheath and then moving the sheath and the instrument together. The position of the sheath and instrument can be tracked while moved together. In some examples, the sheath is implemented as a balloon catheter that includes an expandable member (e.g., a balloon deployable stent or self-expanding stent graft, such as shown in FIG. 7), which can be expanded when positioned at the target site.

FIGS. 5A-5E illustrate an example of using a system 300 for localizing an end of a catheter 302 with respect to a guidewire 304, such as according to the methods of FIG. 3 or 4. The catheter 302 includes a marker band (MB) 306 (e.g., the one or more MBs 114 of FIG. 1) and the guidewire 304 can include a sensors coil 308 (e.g., the one or more sensors 108 of FIG. 1). The MB 306 can be fixed at a known location relative to a distal end of the catheter 302 as to circumscribe the lumen of the catheter. The MB 306 can thus be cylindrical structure of a magnetic shielding material that is applied to an exterior sidewall of the catheter and/or it may be embedded within the catheter sidewall. As used herein, a cylindrical MB structure need not form a complete, solid ring around the lumen to provide sufficient field-influencing effect. Thus, complete or partial ring structures may be used.

Figure 5:
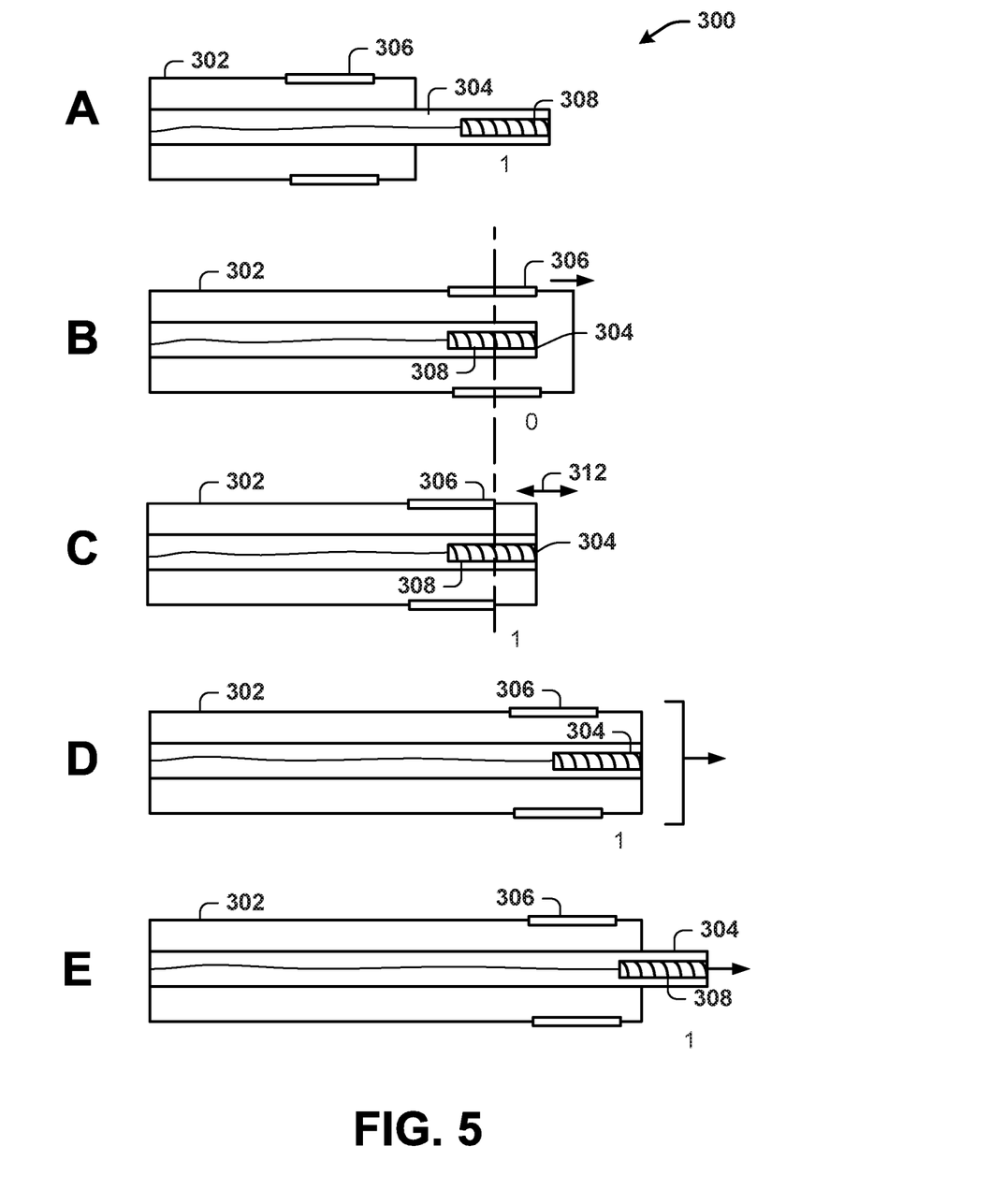

In FIG. 5A, the guidewire 304 can be advanced while its position and orientation is tracked via the sensor coil 308 by the tracking system. In FIG. 5B, the MB 306 is longitudinally advanced to the point where it aligns with the sensor coil 308. For example, the alignment between the sensor coil 308 and the marker band 306 can be demonstrated by a virtual reference plane 310 extending perpendicular the longitudinal axis of each of the guidewire and the sheath also extends through an approximate center of each of the marker band and the sensor. Thus, the marker band 306 concentrically surrounds, and thus shields (e.g., magnetically interferes with) a sufficient portion of the sensor coil 308 (indicated at FIG. 5B as going from a "1" to "0"), such as to shield the sensor from an EM field.

As disclosed herein, the tracking system detects the MB 306 by monitoring for a change in signaling from a first type to a second type from the sensor coil 308 during a transition of the catheter 302 relative to the guidewire 304 corresponding to a first transition. The tracking system can determine a location of the sensor coil 308 when the MB 306 concentrically surrounds, and thus shields (or magnetically interferes with) the sensor coil 308. The tracking system can display a message on a display informing a user that the MB 306 has been detected (even before its position has been localized).

In FIG. 5C, the catheter 302 is retracted (indicated as going from a "0" to "1") and is one of proximal to the reference 310 or the MB 306 is sufficiently distal to the sensor coil (not shown). In going from 5B to 5C, the distal edge of the MB 306 moves from being aligned with the distal edge of the sensor 308 in 5B to aligned with a center of the sensor. This results in removing sufficient influence (e.g., shielding) from the sensor 308 to enable the tracking system to detect the MB 306. For instance, the tracking system can detect the transition in sensor signaling from the second type to the first type provided by the sensor coil 308 during a transition of the catheter 302 relative to the guidewire 304. The tracking system can determine a relative location of the MB 306 of the catheter 302 based on a given distance 312 that the catheter 302 was retracted relative to the guidewire 304 relative to the determined location of sensor coil 308. In this example of FIG. 5C, the distal edge of the catheter 302 is axially aligned with the distal edge of the guidewire. Thus, the tracking system can determine a location of the catheter 302 relative to the guidewire 304. In FIG. 5D, the guidewire 304 and the catheter 302 can now be simultaneously advanced and tracked through an endovascular structure, for example, to a treatment site via the sensor coil 308 of the guidewire 304 based on relative location relationship between the sensor coil 308 and the MB 306. In FIG. 5E, the catheter 302 and the guidewire 304 can be positioned at the treatment site, for example, and the guidewire advanced beyond the distal edge of the catheter 302.

FIGS. 6A-G illustrates an example of using a system 400 that can be used for positioning a balloon deployable stent 402, which is mounted over the distal end of the catheter 406 between marker bands 412 for deployment at a target site 404 (e.g., a lesion) within vasculature of a patient. For example, a guidewire 408 and the catheter 406 can be inserted into a patient during a minimally invasive medical procedure. The guidewire 408 can be advanced through endovascular structures 410 of the patient to the target site 404 under an external EM field. In one example, the endovascular structure 410 is an artery of the patient and the target site 404 is a lesion site.

A tracking system (e.g., tracking system 112, 160) can be employed during to track the location of the guidewire 408 and generate a display (e.g., an icon or other graphical representation) of the guidewire relative to a 3-D anatomical model of the endovascular structure 410. The tracking system can determine an absolute position of the guidewire 408 based on signaling provided from one or more sensors 414 fixed to the distal end of the guidewire. The tracking system further can determine a corresponding location of the catheter 406 relative to the guidewire based on detecting changes in signaling provided by the sensor(s) 414 of the guidewire 408 as the distal end of the catheter 406 is advanced relative to the sensors 414 of the guidewire 408. The tracking system can provide navigational guidance of the catheter 406 and the guidewire 408 during the medical procedure, which can be visualized on the display.

As disclosed herein, for example, the catheter 406 includes marker bands (MBs) 412 (e.g., the one or more MBs 114 or 157) and the guidewire 408 includes EM sensors 414 (e.g., the one or more sensors 108 or 154). In one example, spacing between the pair of MBs 412 can differ from spacing between the pair of the sensor 414. Differing the spacing can ensure that each sensor 414 is not simultaneously influenced (e.g., by shielding or magnetically interfering) by a respective MB 412. In this example, the catheter 406 further includes a deployable stent 402. The deployable stent 402 can positioned between the pair of MBs 412, for example.

In FIG. 6A, the guidewire 408 is advanced across the target site 404 and is kept in position relative to the site. In FIG. 6B, the catheter 406 is advanced along the guidewire 406 to a point where a distal one of the MBs 412 is axially aligned as and concentrically surrounds a given sensor 414, and thus shields or magnetically interferes with a sufficient portion the sensor (indicated in FIG. 3B as going from a "1" to "0" on the proximal sensors 414). The tracking system detects the distal MB 412 by monitoring for a change in signaling from a first type to a second type from the proximal sensor 414 during a transition of the catheter 406 relative to the guidewire 408 corresponding to a first transition in the sensor signal. The tracking system can determine a location of the proximal sensor 414 in response to detecting a signaling transition that occurs when the distal MB 412 concentrically surrounds, and thus shields or magnetically interferes with a sufficient portion of the proximal sensor 414.

In FIG. 6C, the catheter 406 can be subsequently advanced further along the guidewire 408 to a point where the distal MB 412 is sufficiently offset from the proximal sensor 414 (indicated in as going from a "0" in 6B to "1" in 6C at the proximal sensor 414, such that sensors provide localizable sensor signals, demonstrated at "1"). The tracking system can detect when the distal MB 412 is not substantially interfering with the proximal sensor 414 by monitoring for a change in signaling from the second type of signaling to the first type of signaling provided by the proximal sensor 414 in response to a transition of the catheter 406 relative to the guidewire 408 corresponding to a second transition. The tracking system can determine a location of the distal MB 412 relative to the proximal sensor 414 based on a transition difference between the first transition and the second transition from the determined location of the proximal sensor 414. Thus, the tracking system can localize the distal MB 412 relative to the proximal sensor 414.

Figure 6:
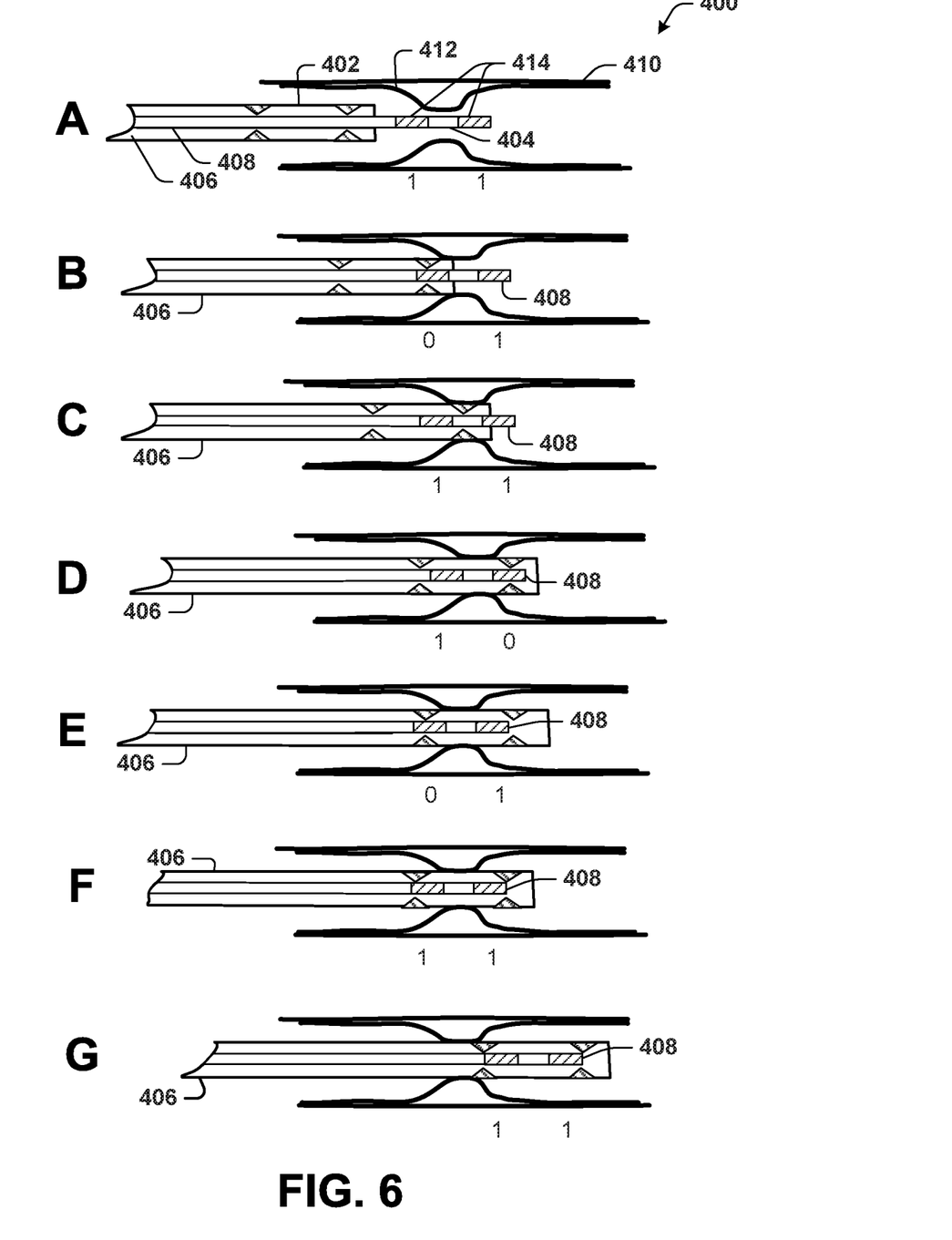

In FIG. 6D, the catheter can be advanced further along the guidewire to a point where the distal-most MB 412 is aligned with and thus shields or magnetically interferes with a sufficient portion of a distal sensor 414 of the pair of sensors coils 414 (indicated in FIG. 6 as going from a "1" in 6C to "0" in 6D for the distal sensor coil). The tracking system can detect the distal MB 412 by monitoring for a change in signaling from a third type to a fourth type from the distal sensor 414 in response to a transition of the catheter 406 relative to the guidewire 408 corresponding to a third transition.

In FIG. 6E, the catheter 406 can be subsequently advanced further along the guidewire 408 to a point where the distal MB 412 is sufficiently offset from the distal sensor 414 (indicated in FIG. 6 as going from a "0" in 6D to "1" in 6E on the distal sensor 414). Also in FIG. 6E, the proximal MB 412 is aligned with the proximal sensor 414, which corresponds to a transition from "1" in FIG. 6D to a "0" in 6E. The tracking system thus can localize the distal MB 412 relative to the distal sensor 414 and, in turn derive the position of the distal end of the catheter itself. Additionally or alternatively, the tracking system can localize a proximal MB 412 relative to the proximal sensor 414 using a localizing method as disclosed herein. In FIG. 6F, the catheter 406 can be maneuvered (retracted) relative to the guidewire 408 to position both MBs 412 offset from both sensors 414, such that both sensors reside between the MBs and both sensors receive sufficient EM field to be localized. In this position, the catheter 406 and the guidewire can be fixed together and moved in the vasculature. The balloon deployable stent 402, which also is between the MBs, can also localized moved to an appropriate location corresponding to the treatment site 404 for deployment based on the position of the sensors determined by the tracking system. In FIG. 6G, the catheter 406 and the guidewire 408 can be simultaneously advanced while maintaining a fixed relationship relative to one another. The determined location of the catheter can be visualized on a display concurrently with the guidewire and patient anatomy to provide real-time intraoperative guidance.

FIG. 7 depicts a cross-sectional view of an example system 500 that includes a sheath 502 and an elongated instrument 504, such as a guidewire. Each of the sheath 502 and guidewire 504 can have a configuration as disclosed herein (FIGS. 1-6). Briefly stated, the guidewire 504 includes sensors 506, 508 spaced longitudinally apart from each other at a distal end thereof the guidewire. The distal end 510 may be straight (as shown) or curved with respect to a central longitudinal axis 518, which extends through the illustrated distal ends of both the guidewire 504 and catheter 502. An electrical connection (not shown) extends from the sensor to a proximal end of the instrument to communicate a sensor signal to a tracking system, as disclosed herein, in response to the sensor detecting an electromagnetic field. The sheath 502 includes a lumen extending longitudinally through a cylindrical body of the sheath between spaced apart ends thereof. The sheath terminates in a distal edge 516. The lumen is dimensioned to permit axial movement of the instrument relative to the sheath within the lumen. In the example, of FIG. 7, the lumen is provided with a much larger diameter than the outer diameter of the guidewire 504.

The sheath includes marker bands 512 and 514 proximal the distal end of the sheath. As mentioned, the marker band is adapted to interfere with or enable the detection of the electromagnetic field by the sensor depending on an extent of axial alignment between the marker band and the sensor. Because of the larger diameter difference and potential radial distance between a given MB 512, 514 and sensor 506, 508, the MB is configured as a magnetic type of MB having a shape to help focus its magnetic filed radially inward. For example, each of the magnetic type MBs 512, 514 is tapered so that a radially outer surface is wider than a radially inner surface thereof (e.g., providing a trapezoidal cross-sectional shape). Tapering the magnetic type MBs operates to help focus a magnetic field of the magnetic type MBs radially inwardly enabling use when the distance between MBs 512, 514 and sensors 506, 508 is greater. The influence by magnetic field strength of the magnetic type MBs on the sensors will thus depend on a diameter of the catheter 502. A catheter 502 with a larger diameter will require magnetic type MBs that have a greater magnetic field strength in contrast to a device 102 with a smaller diameter catheter. However, to maximize the influence by the MBs 512, 514 on the sensors 506, 508, the radial distance between the marker band 114 and the sensor should be minimized to the extent practical.

In the example of FIG. 7, the catheter 502 includes an expandable member (e.g., a balloon) 520 and a deployable stent 522 disposed around the distal end of the catheter 502 in a compressed state. By positioning the stent 522 between a pair of MB's, for example, the tracking system can localize the stent 522 with respect to a pair of adjacent sensors for positioning and provide guidance (e.g., a 3D visualization) for deploying the stent at a desired target site, such as explained with respect to the example of FIG. 6. For example, at the target site, the distal end of the catheter 502 can be located in 3D space relative to the guidewire and the target site as to position the expandable member 520 properly across the target site for deployment (e.g., inflation of the balloon and corresponding expansion of the stent and/or graft).

What have been described above are examples. It is, of course, not possible to describe every conceivable combination of components or methods, but one of ordinary skill in the art will recognize that many further combinations and permutations are possible. Though certain components described herein are shown as having specific geometric shapes, all structures of this disclosure may have any suitable shapes, sizes, configurations, relative relationships, cross-sectional areas, or any other physical characteristics as desirable for a particular application. Additionally, it is to be understood that the Figures herein are not necessarily to scale but simplified to demonstrate the principles of this disclosure. Accordingly, the invention is intended to embrace all such alterations, modifications, and variations that fall within the scope of this application, including the appended claims. As used herein, the term "includes" means includes but not limited to, the term "including" means including but not limited to. The term "based on" means based at least in part on. Additionally, where the disclosure or claims recite "a," "an," "a first," or "another" element, or the equivalent thereof, it should be interpreted to include one or more than one such element, neither requiring nor excluding two or more such elements.

What is claimed is:

1. A system comprising:
   a tracking system configured to generate an electromagnetic field;
   an elongated instrument including at least one sensor at a distal end thereof and an electrical connection extending from the sensor to a proximal end of the instrument to communicate a sensor signal to the tracking system in response to the sensor detecting the electromagnetic field;
   an elongated sheath having a lumen extending longitudinally through spaced apart distal and proximal ends thereof, the lumen dimensioned to permit axial movement of the instrument relative to the sheath within the lumen, the sheath including at least one marker band proximal the distal end of the sheath that circumscribes the sheath, the at least one marker band adapted to influence the detection of the electromagnetic field by the at least one sensor depending on an extent of axial alignment between the marker band and the sensor, wherein the marker band comprises a cylindrical body of a magnetic or magnetic shielding material to interfere with the detection, wherein the tracking system provides tracking data based on the sensor signal; and
   a location calculator that determines an absolute three-dimensional position of the sheath based on the tracking data, in which the tracking data represents a location of the sensor in a tracking coordinate system of the tracking system based on the sensor signal in the absence of the influence of the marker band, and represents changes in the sensor signal based on the influence of the marker band on the detection of the electromagnetic field.

2. The system of claim 1, wherein the cylindrical body has a tapered cross section extending from an outer surface and tapering to a radially inner surface.

3. The system of claim 1,
   wherein the instrument includes at least two sensors spaced axially apart from each other on the distal end thereof, and
   wherein the sheath includes at least two marker bands spaced axially apart from each other proximal the distal end thereof.

4. The system of claim 3, wherein the spacing between an adjacent pair of the sensors along the instrument is different from the spacing between an adjacent pair of the marker bands along the sheath.

5. The system of claim 3, wherein a direction of the sheath is determined relative to the instrument while the instrument is being retracted or advanced relative to the sheath.

6. The system of claim 1, wherein the changes in the sensor signal for each sensor include:

a first transition in the sensor signal being representative of detecting the electromagnetic field to the sensor signal being representative of interference with detecting the electromagnetic field; and a second transition in the sensor signal being representative of the interference with detecting the electromagnetic field to the sensor signal being representative of again detecting the electromagnetic field.

7. The system of claim 6, further comprising an output generator that provides a message to indicate detection of the first transition, corresponding to detection of the marker band being aligned with the sensor, the location calculator determining the position of the sheath relative to the instrument in the tracking coordinate system based on the tracking data in response to detecting the second transition with predefined movement of sheath relative to the instrument that provides the second transition.

8. The system of claim 6, wherein the at least one sensor comprises a distal sensor and a proximal sensor and the at least one marker band comprises a distal marker band and a proximal marker band, the tracking data comprises multi-sensor tracking data representing a respective position and orientation in the tracking coordinate system for each of a plurality of sensors disposed on the instrument, and
wherein a relative axial spacing between the sensors and between the marker bands is configured to prevent the marker bands from being axially positioned to circumscribe all of the sensors concurrently and thereby enable the tracking system to determine the location of at least one of the sensors continuously.

9. The system of claim 1, wherein the tracking system provides the tracking data as a plurality of frames representing a location of the at least one sensor at discrete times, the tracking data for each of the plurality of frames of including a position and an orientation for the at least one sensor in the tracking coordinate system.

10. The system of claim 1, further comprising an output generator to generate a graphical visualization representing the location of the instrument and the location of the sheath with respect to a graphical representation of an anatomical structure.

11. The system of claim 10, wherein the graphical representation of anatomical structure is generated based on image data acquired for a patient.

12. The system of claim 1, wherein the instrument is a guidewire, the sensor comprising a sensor coil that enables at least tracking in at least five degrees of freedom.

13. A system comprising:
a guidewire including at least one sensor at a distal end thereof and an electrical connection extending from the sensor to communicate a sensor signal in response to the sensor detecting an electromagnetic field;
an elongated sheath having a lumen extending longitudinally through spaced apart distal and proximal ends thereof, the lumen dimensioned to permit axial movement of the instrument relative to the sheath within the lumen, the sheath including at least one marker band proximal the distal end of the sheath that circumscribes the sheath, wherein the marker band comprises a cylindrical body of a magnetic shielding material or a magnetic material and the marker band is adapted to influence the detection of the electromagnetic field by the at least one sensor depending on an extent of axial alignment between the marker band and the sensor;
a tracking system configured to generate the electromagnetic field, and the tracking system is configured to provide tracking data based on the sensor signal;
a location calculator that determines an absolute three-dimensional location of the sheath within a tracking coordinate system of the tracking system based on the tracking data, in which the tracking data represents a location of the sensor in a tracking coordinate system based on the sensor signal in the absence of the influence of the marker band, and represents changes in the sensor signal based on the influence of the marker band on the detection of the electromagnetic field; and
an output generator to generate a graphical visualization representing the location of the guidewire and the location of the sheath with respect to a graphical representation of an anatomical structure.

14. The system of claim 13, wherein the changes in the sensor signal for each sensor include:
a first transition in the sensor signal provided in response to detecting the electromagnetic field to the sensor signal provided in response to interference with detecting the electromagnetic field; and
a second transition in the sensor signal provided in response to interference with detecting the electromagnetic field to the sensor signal provided in response to detecting the electromagnetic field.

15. The system of claim 14, wherein the output generator provides a message to indicate detection of the first transition, corresponding to when the sheath circumscribes with the sensor, the location calculator determining the position of the sheath relative to the guidewire in the tracking coordinate system based on the tracking data in response to detecting the second transition with predefined movement of sheath relative to the guidewire that provides the second transition.

16. The system of claim 13,
wherein the sensor further comprises a distal sensor and a proximal sensor,
wherein the marker band further comprises a distal marker band and a proximal marker band, and
wherein relative axial spacing between the sensors and between the marker bands is configured to prevent the marker bands from being axially positioned to circumscribe all of the sensors concurrently and thereby enable the tracking system to determine the location of at least one of the sensors continuously.

17. The system of claim 16, wherein the tracking system provides the tracking data to include multi-sensor tracking data representing a position and orientation of the plurality of sensors disposed on the guidewire in tracking coordinate system.

18. The system of claim 13, wherein the tracking system provides the tracking data as a plurality of frames representing a location of the at least one sensor at discrete times, the tracking data for each of the plurality of frames of including a position and an orientation for the instrument in the tracking coordinate system.

19. The system of claim 13, wherein the cylindrical body includes the magnetic material, the cylindrical body having a tapered cross section extending from an outer surface and tapering to a radially inner surface.

\* \* \* \* \*